United States Patent
Roy

(10) Patent No.: US 10,631,864 B2
(45) Date of Patent: Apr. 28, 2020

(54) MINIMALLY TRAUMATIC ANASTOMOSIS

(71) Applicant: ANASTOMOSIS AS, Stavanger (NO)

(72) Inventor: Sumit Roy, Hafrsfjord (NO)

(73) Assignee: ANASTOMOSIS AS, Stavanger (NO)

(*) Notice: Subject to any disclaimer, the term of this patent is extended or adjusted under 35 U.S.C. 154(b) by 305 days.

(21) Appl. No.: 15/502,375

(22) PCT Filed: Aug. 11, 2015

(86) PCT No.: PCT/EP2015/068474
§ 371 (c)(1),
(2) Date: Feb. 7, 2017

(87) PCT Pub. No.: WO2016/023907
PCT Pub. Date: Feb. 18, 2016

(65) Prior Publication Data
US 2017/0231634 A1 Aug. 17, 2017

Related U.S. Application Data

(60) Provisional application No. 62/036,345, filed on Aug. 12, 2014.

(51) Int. Cl.
*A61B 17/11* (2006.01)
*A61F 2/07* (2013.01)
*A61F 2/958* (2013.01)

(52) U.S. Cl.
CPC ............... *A61B 17/11* (2013.01); *A61F 2/07* (2013.01); *A61F 2/958* (2013.01);
(Continued)

(58) Field of Classification Search
CPC ............. A61B 17/11; A61B 17/1114; A61B 2017/1132; A61B 2017/1135;
(Continued)

(56) References Cited

U.S. PATENT DOCUMENTS 5,695,504 A * 12/1997 Gifford, III .......... A61B 17/064
606/139
5,921,995 A * 7/1999 Kleshinski ............... A61F 2/07
606/153

(Continued)

FOREIGN PATENT DOCUMENTS

DE   10 2008 055 587   8/2009
WO      98/16174        4/1998
(Continued)

OTHER PUBLICATIONS

International Search Report dated Feb. 8, 2012 in corresponding International (PCT) Application No. PCT/EP2015/068474.

*Primary Examiner* — Katrina M Stransky
(74) *Attorney, Agent, or Firm* — Wenderoth, Lind & Ponack, L.L.P.

(57) ABSTRACT

An anastomosis prosthesis comprising a tubular member with a leading end comprising a leading edge, and a trailing end comprising a trailing edge, wherein the leading end of the tubular member is reversibly, radially compressible, and the leading edge of the tubular member is provided with one or more radially outwardly directed flexible, substantially linear anchoring members. The anchoring members are initially arranged at an angle in relation to a longitudinal axis of the tubular member such that the anchoring members point in the direction of the trailing end of the tubular member.

8 Claims, 15 Drawing Sheets

(52) U.S. Cl.
CPC ............... *A61B 2017/1107* (2013.01); *A61B 2017/1132* (2013.01); *A61B 2017/1135* (2013.01); *A61B 2017/1139* (2013.01); *A61F 2220/0008* (2013.01)

(58) Field of Classification Search
CPC .... A61B 2017/1139; A61B 2017/1103; A61B 2017/1107; A61F 2220/0008
See application file for complete search history.

(56) References Cited

U.S. PATENT DOCUMENTS

| | | |
|---|---|---|
| 6,241,743 B1 | 6/2001 | Levin et al. |
| 6,485,513 B1 | 11/2002 | Fan |
| 7,063,711 B1 | 6/2006 | Loshakove et al. |
| 2002/0049459 A1* | 4/2002 | Kato ............... A61B 17/11 606/153 |
| 2003/0065385 A1 | 4/2003 | Weadock |
| 2004/0068279 A1 | 4/2004 | Hindrichs et al. |
| 2010/0023132 A1 | 1/2010 | Imran |

FOREIGN PATENT DOCUMENTS

| | | |
|---|---|---|
| WO | 00/56226 | 9/2000 |
| WO | 01/26562 | 4/2001 |
| WO | 2007/029989 | 3/2007 |
| WO | 2012/117402 | 9/2012 |

* cited by examiner

Fig. 4
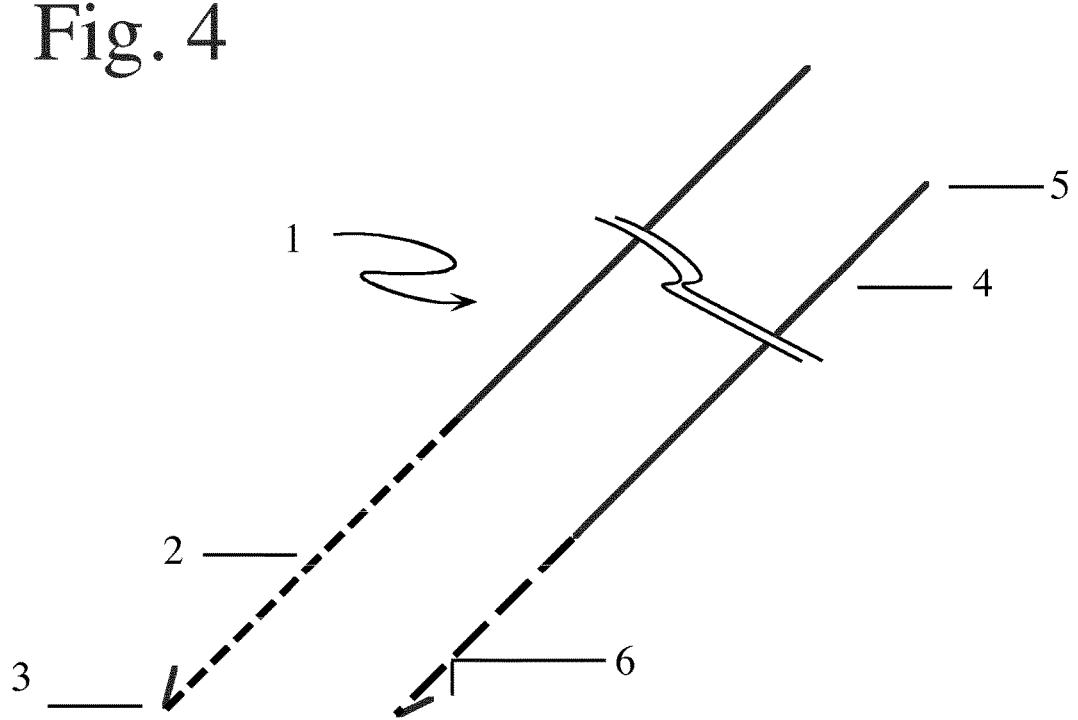
Fig. 5a    Fig. 5b
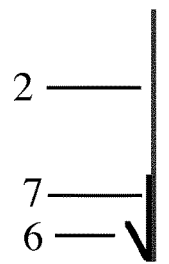 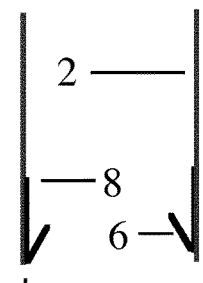
Fig. 6a
Fig. 6b
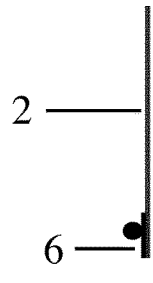 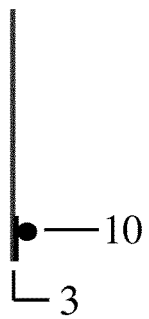   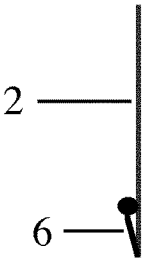 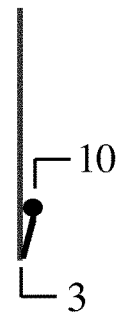

Fig. 7
Fig. 8
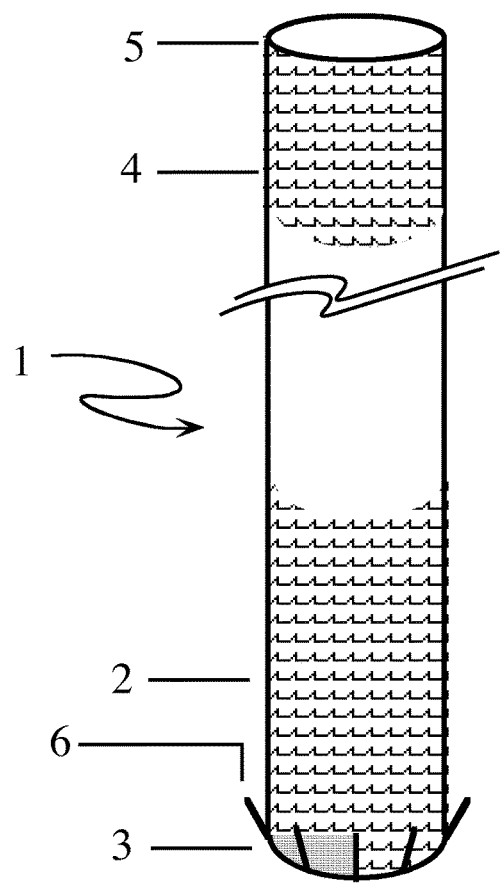
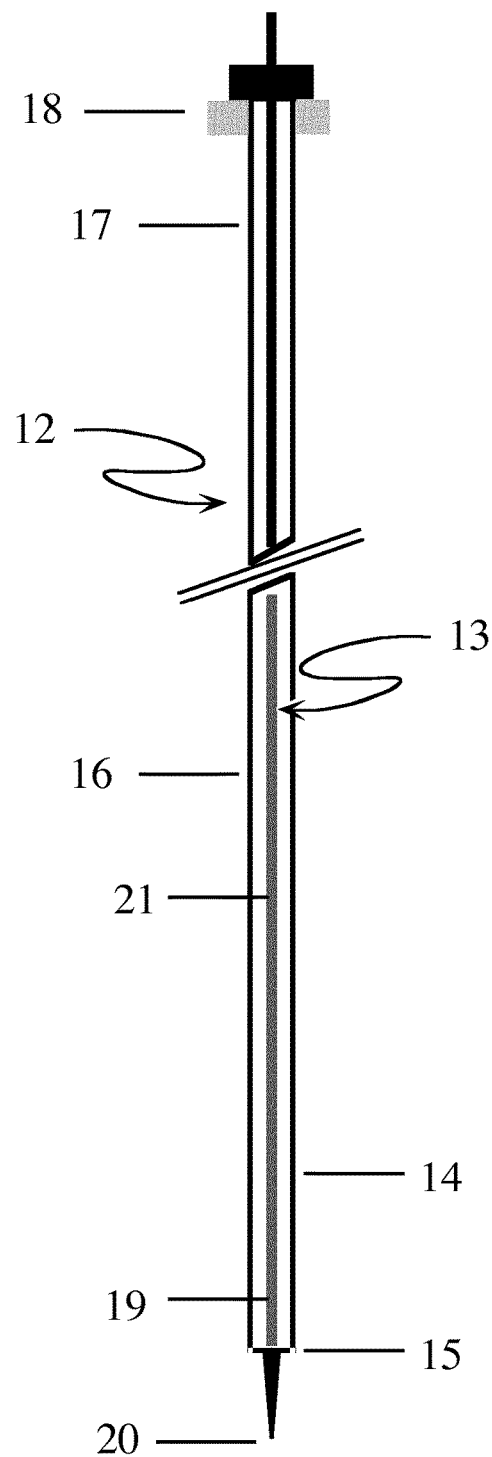

Fig. 11
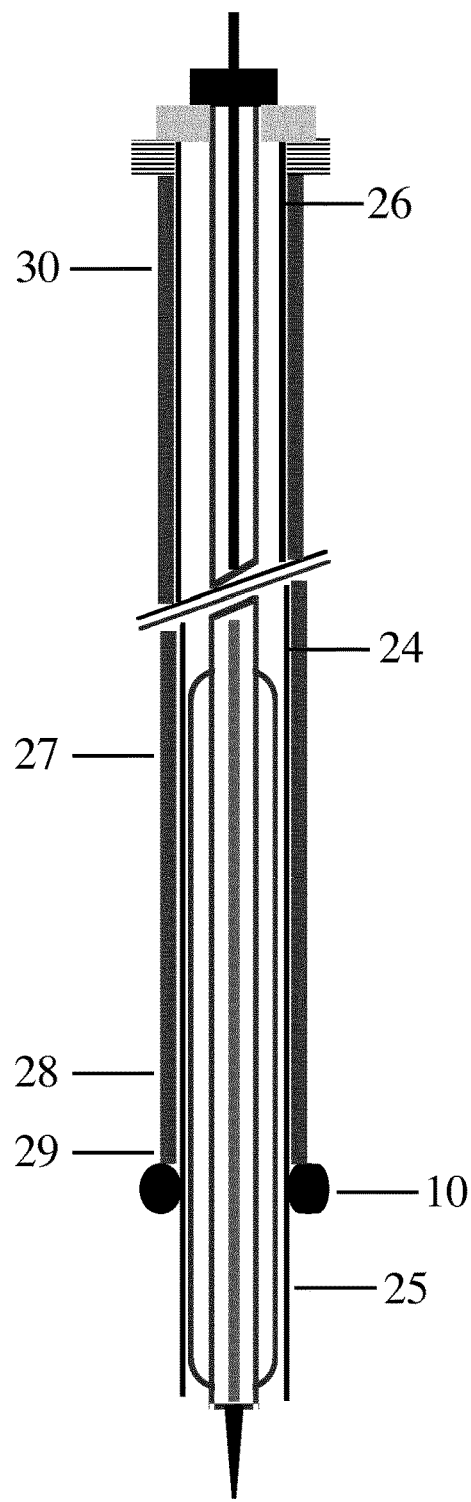
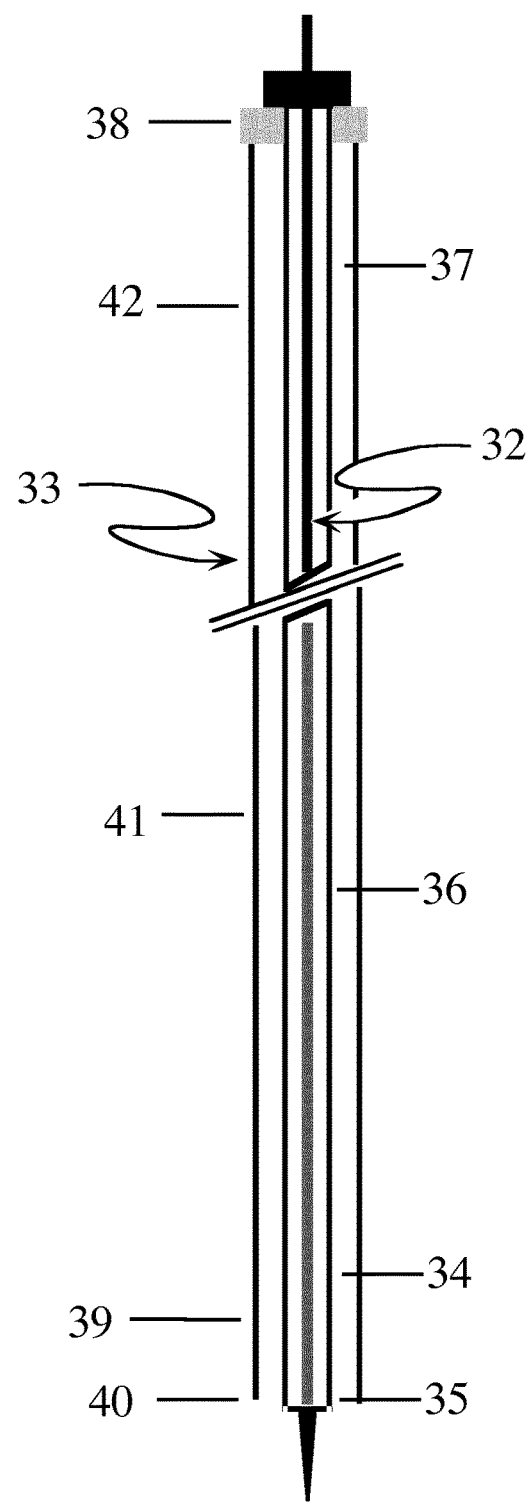
Fig. 12

Fig. 13
Fig. 14
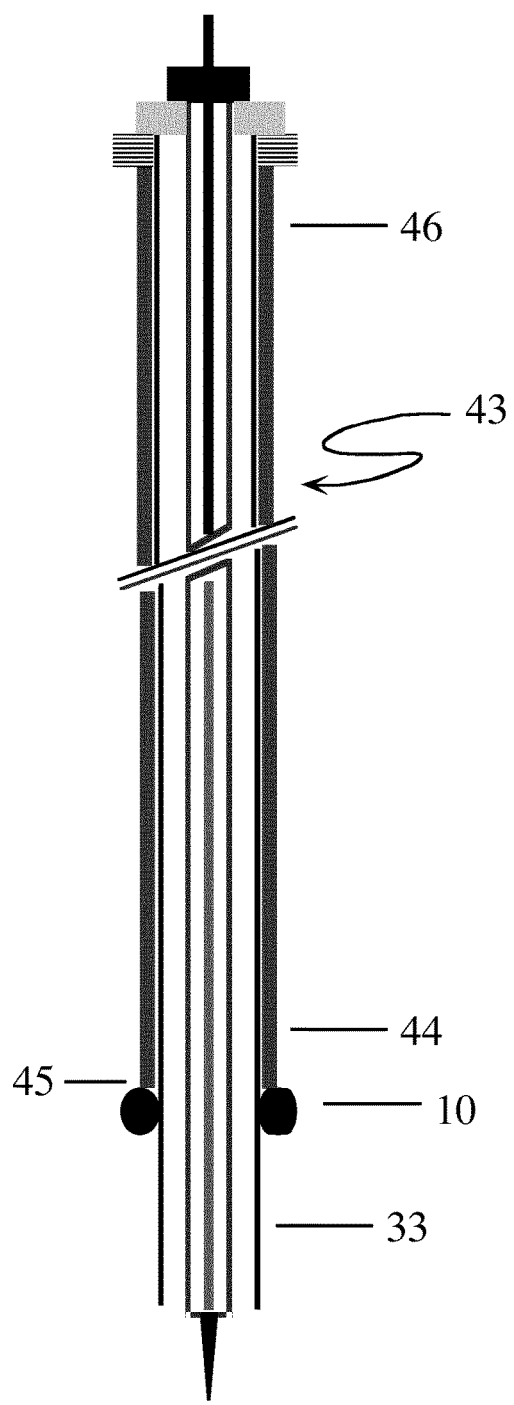
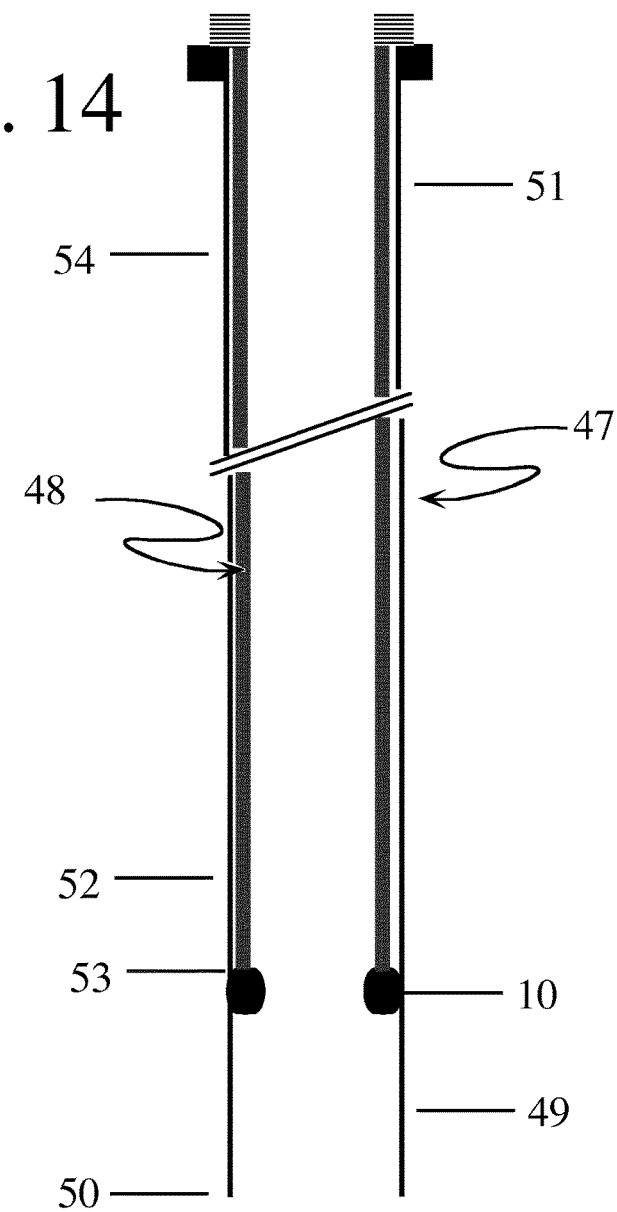
Fig. 15
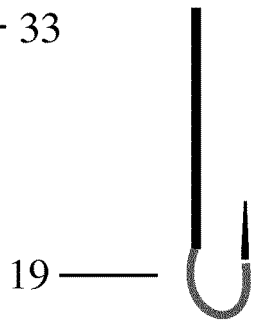

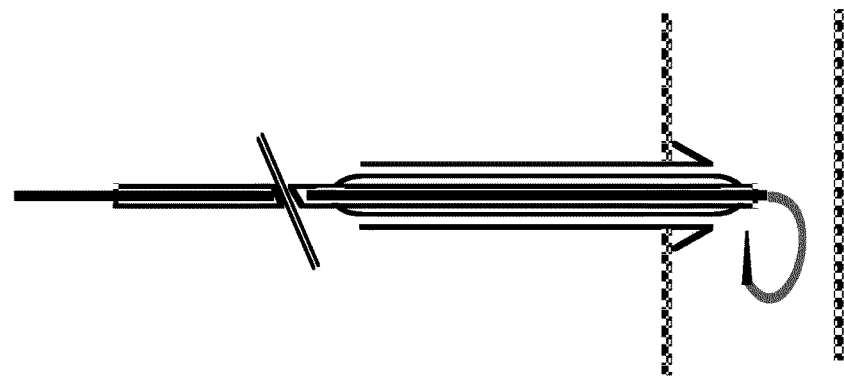
Fig. 19
Fig. 20
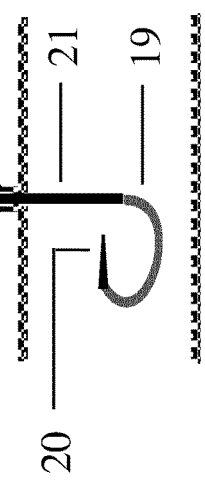
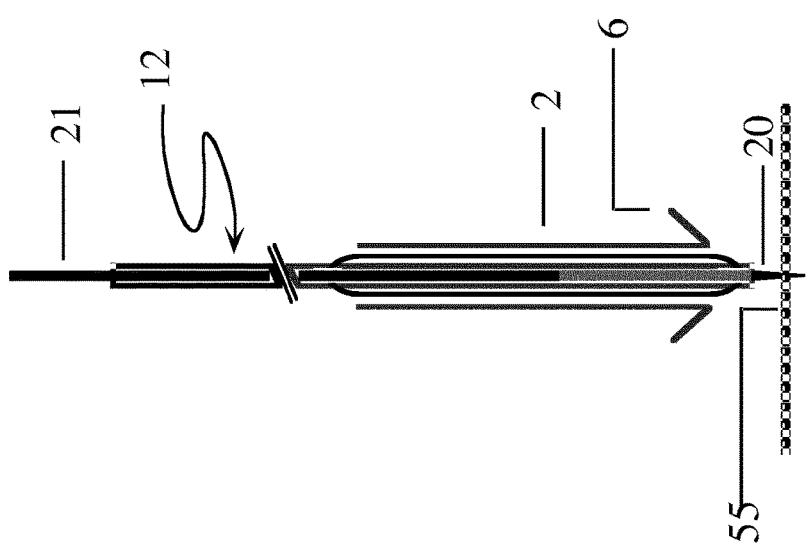
Fig. 18

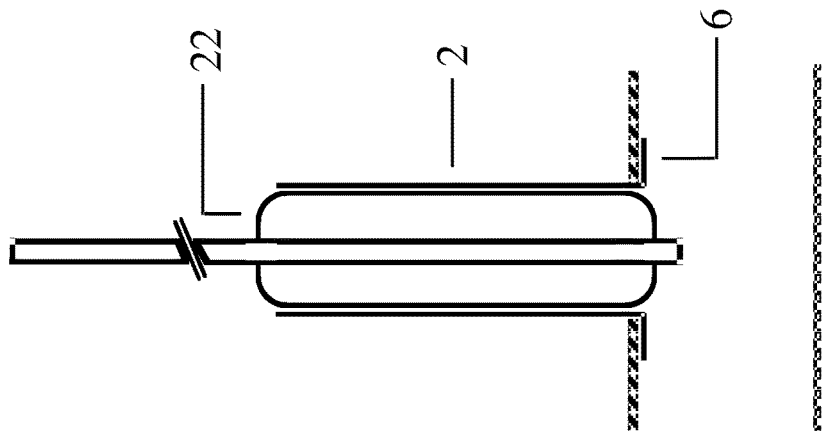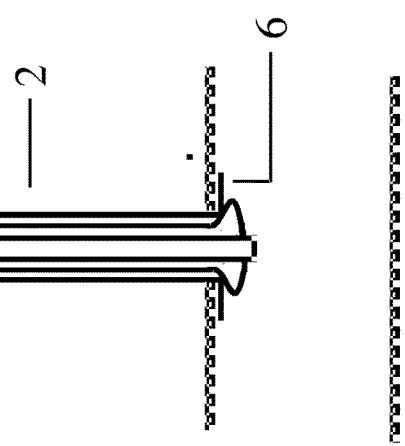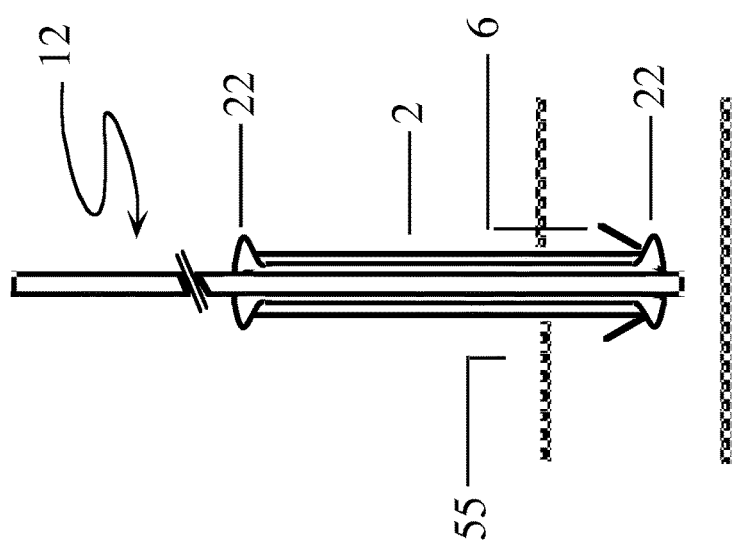

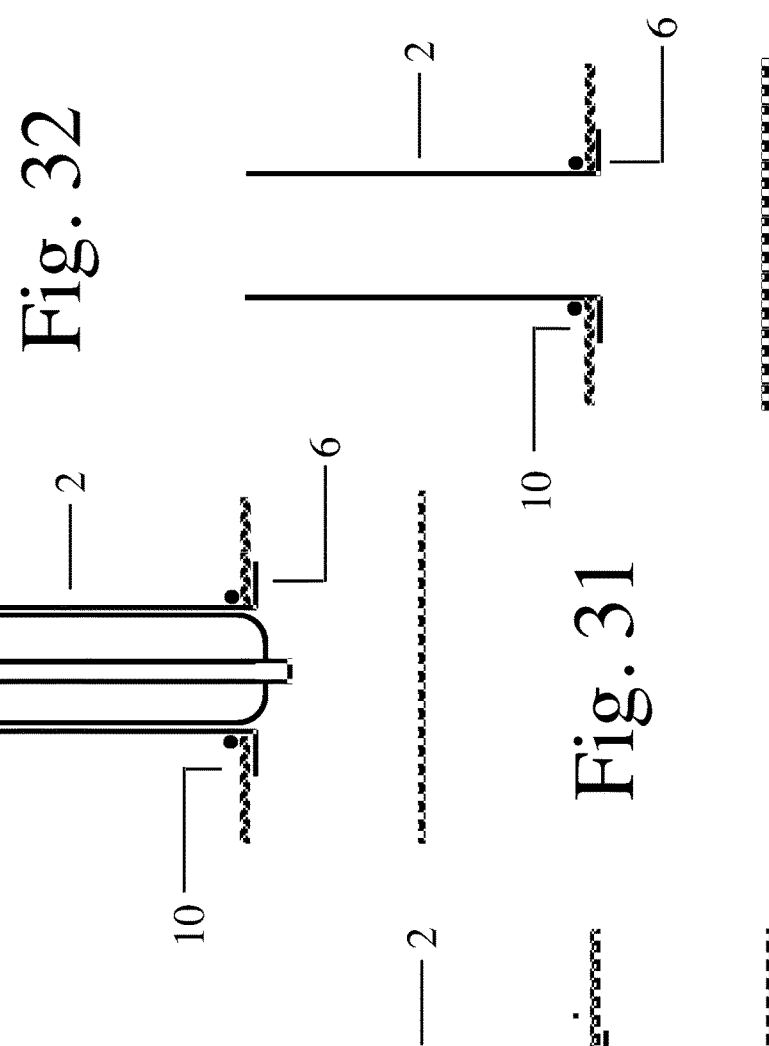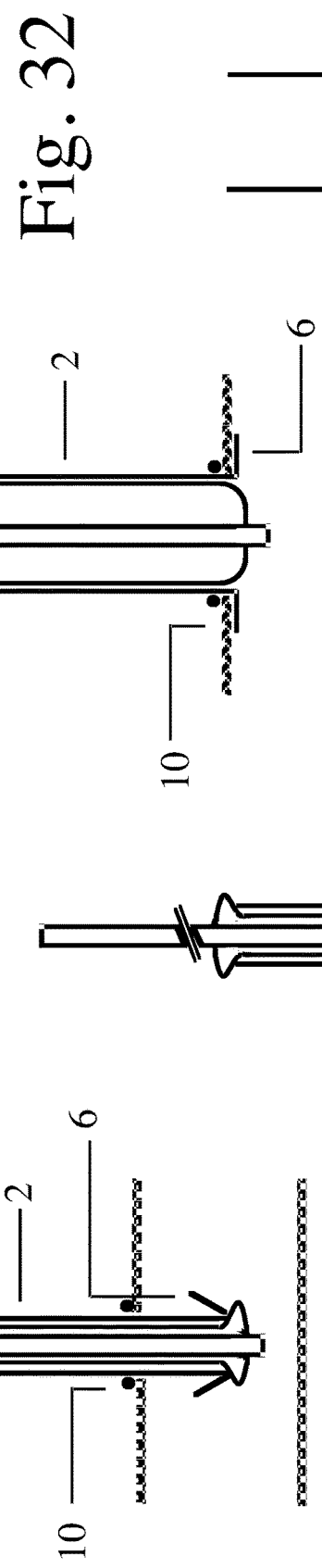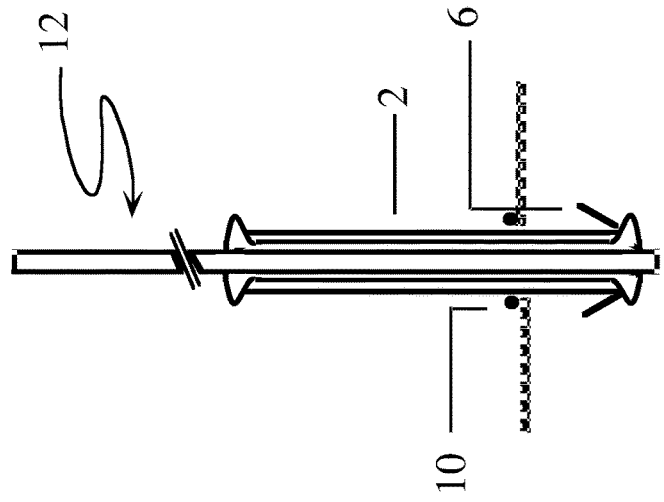

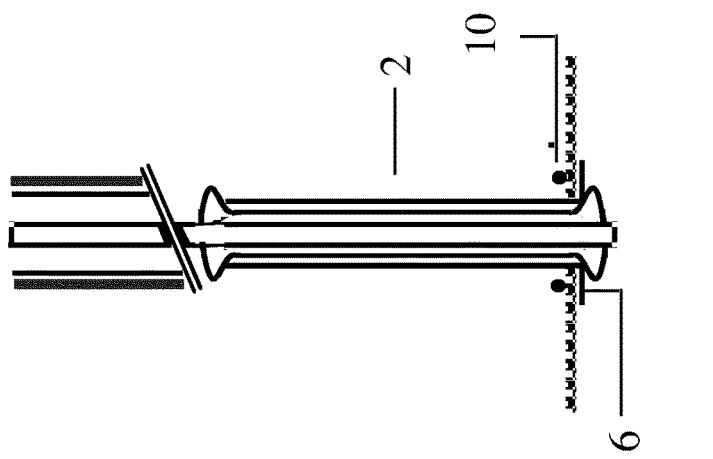
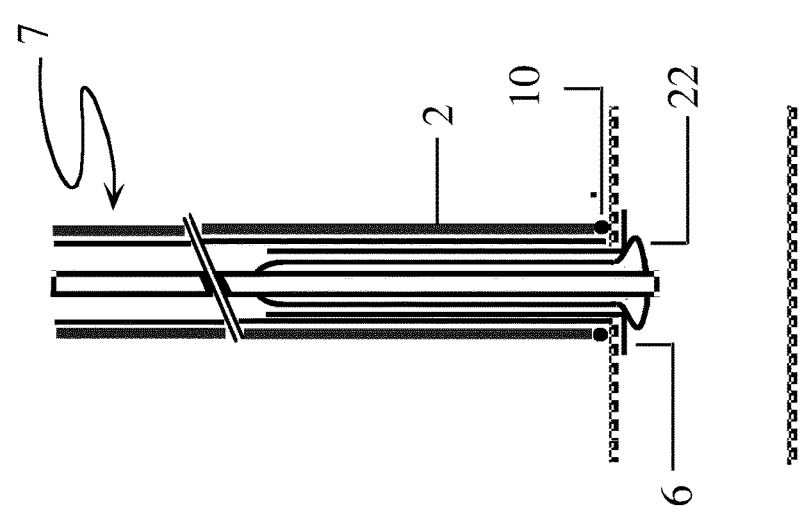
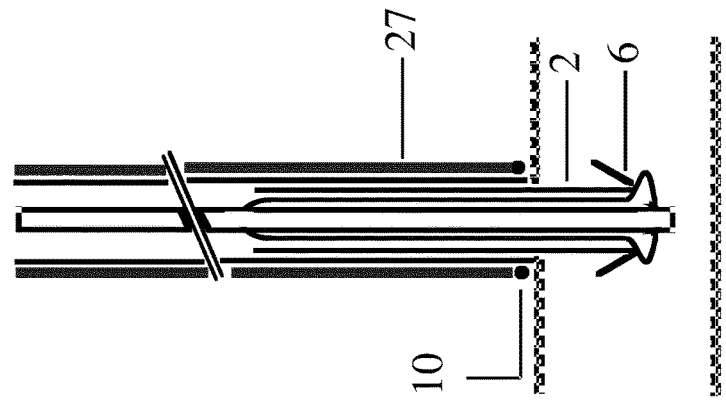

MINIMALLY TRAUMATIC ANASTOMOSIS

RELATED APPLICATION

The patent application claims priority from U.S. Provisional Patent Application Ser. No. 62/036,345, filed on Aug. 12, 2014, the entire disclosure of the application being expressly incorporated herein by reference.

TECHNICAL FIELD

The invention relates to a method for interconnection of and fluid communication end-to-side between a tubular organ such as a blood vessel, and a synthetic substitute such as a vascular graft.

BACKGROUND

The ability to create structurally sound, geometrically, optimal end-to-side connections ("anastomosis") between blood vessels and synthetic blood vessel substitutes ("vascular grafts") is one of the keys to therapeutic success in vascular surgery. Currently a vascular graft is usually anastomosed to a blood vessel by stitching them together. Creating anastomoses thus, though far from optimal, has stood the test of time. However the method is singularly unsuited for using a "minimally invasive" approach, such as for example laparoscopic surgery.

Over the years innumerable devices for creating end-to-side anastomoses without stitching have been disclosed in the patent literature including U.S. Pat. No. 2,127,903 (Bowen) U.S. Pat. No. 3,155,095 (Brown) U.S. Pat. No. 3,620,218 (Schmitt et al.) U.S. Pat. No. 3,683,926 (Suzuki) U.S. Pat. No. 4,214,586 (Mericle) U.S. Pat. No. 4,366,819 (Castor) U.S. Pat. No. 4,368,736 (Castor) U.S. Pat. No. 4,470,415 (Wozniak) U.S. Pat. No. 4,675,008 (Tretbar) U.S. Pat. No. 4,512,761 (Raible) WO 97/27898 (Evard et al.) U.S. Pat. No. 4,552,148 (Hardy, Jr. et al.) U.S. Pat. No. 4,753,236 (Healy) U.S. Pat. No. 4,769,029 (Patel) U.S. Pat. No. 4,851,001 (Taheri) U.S. Pat. No. 4,816,028 (Kapadia et al.) U.S. Pat. No. 4,957,499 (Lipatov et al.) U.S. Pat. No. 5,156,691 (Ehrenfeld) U.S. Pat. No. 5,123,908 (Chen) U.S. Pat. No. 5,192,289 (Jessen) U.S. Pat. No. 5,250,058 (Miller) U.S. Pat. No. 5,222,963 (Brinkerhoff et al.) U.S. Pat. No. 5,330,490 (Wilk et al.) U.S. Pat. No. 5,364,389 (Anderson) U.S. Pat. No. 5,399,352 (Hanson) U.S. Pat. No. 5,425,738 (Gustafson et al.) U.S. Pat. No. 5,425,739 (Jessen) U.S. Pat. No. 5,443,497 (Venbrux) U.S. Pat. No. 5,445,644 (Pietra☐tta et al.) U.S. Pat. No. 5,456,712 (Maginot) WO 00/72764 (Stevens et al.) U.S. Pat. No. 5,456,714 (Owen) U.S. Pat. No. 5,503,635 (Sauer et al.) U.S. Pat. No. 5,509,902 (Raulerson) U.S. Pat. No. 6,179,849 (Yencho et al.) U.S. Pat. No. 6,024,748 (Manzo) U.S. Pat. No. 6,152,937 (Peterson), and U.S. Pat. No. 5,113,621 (Swanson et al.). However only two devices are commercially devices for anastomosing a vascular graft to a blood vessel: Spyder® (Medtronic) and AnastoClip® VCS™ (LeMaitre Vascular). Anastomosing with the Spyder® device is performed with small self-closing nitinol helices that mimic needle and thread. AnastoClips (previously marketed as "Vessel Closure System" [VCS]) are small titanium clips, which have to be manually placed meticulously one at a time to secure a vascular graft to a blood vessel. Thus, in the context of minimally invasive surgery, neither Spyder® nor AnastoClip® VCS™ represent a radical improvement over the conventional practice of manual stitching. Therefore a need still exists for a device for creating end-side anastomoses that is suitable for use during minimally invasive surgery.

BRIEF DESCRIPTION OF THE DRAWINGS

FIG. 4 is a longitudinal cross-sectional view of an anastomosis prosthesis wherein the plane defined by the leading end is not perpendicular to the longitudinal axis of the prosthesis.

FIGS. 5a and 5b represent longitudinal cross-sectional views of the leading end of an anastomosis prosthesis with external collar.

FIGS. 6a and 6b represent longitudinal cross-sectional views of the leading end of an anastomosis prosthesis sealing ring.

FIG. 7 is a perspective transparent view of an anastomosis prosthesis with radially compressible trailing end.

FIGS. 8-13 are longitudinal cross-sectional views of instruments for performing anastomosis with a prosthesis.

FIG. 14 represents cross-sectional view of an anastomosis prosthesis.

FIG. 15 shows a needle wire to be used in a deployment instrument.

FIGS. 18-41 are longitudinal cross-sections illustrating different methods for performing anastomosis with a prosthesis.

SUMMARY

An anastomosis prosthesis comprising a tubular member with a leading end comprising a leading edge, and a trailing end comprising a trailing edge, wherein the leading end of the tubular member is reversibly, radially compressible, and the leading edge of the tubular member is provided with one or more radially outwardly directed flexible, substantially linear anchoring members. The anchoring members are initially arranged at an angle in relation to a longitudinal axis of the tubular member such that the anchoring members point in the direction of the trailing end of the tubular member.

DETAILED DESCRIPTION

For the purposes of promoting an understanding the invention, reference will be made to some embodiments and one application of said invention, and specific language will be used to for the purpose. It will nevertheless be understood that no limitation of the scope of the invention is thereby intended. Alterations and further modifications of the inventive features described herein, and additional applications of the principles of the invention which would occur to one skilled in the relevant art and having possession of this disclosure, are to be considered within the scope of the invention.

Figure 1:
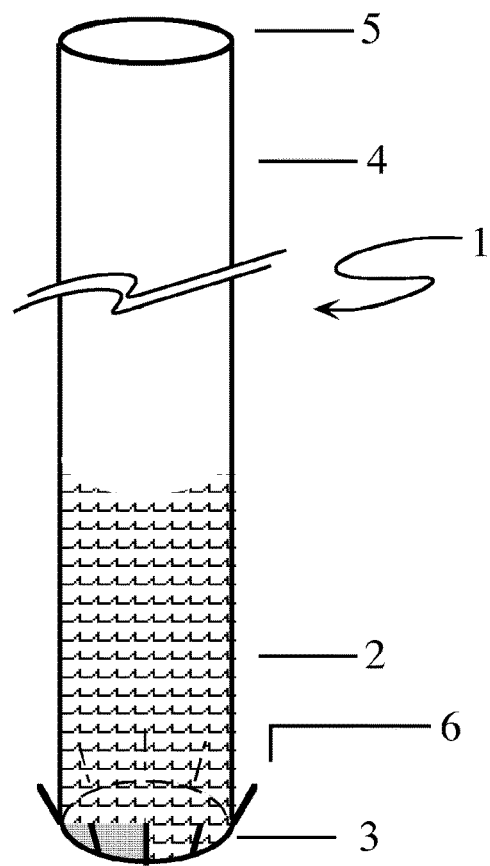
FIG. 1 is a perspective transparent view of an anastomosis prosthesis.
Figure 2:
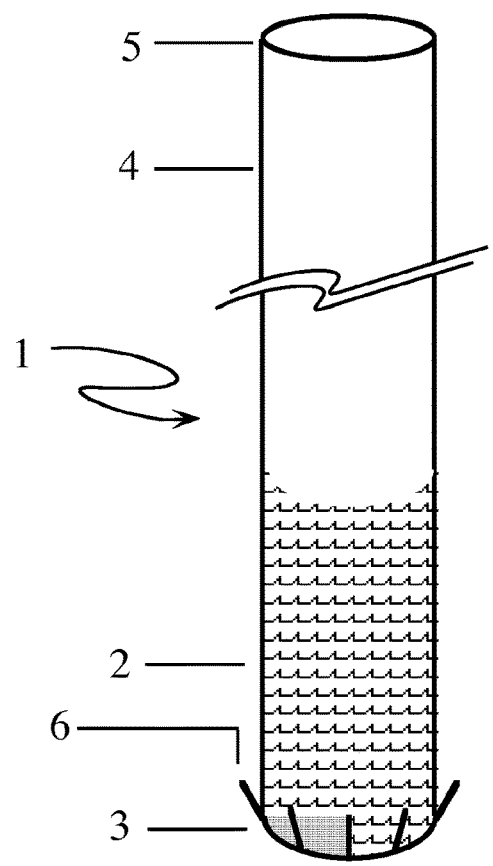
FIG. 2 is a perspective transparent view of an anastomosis prosthesis.
Figure 3:
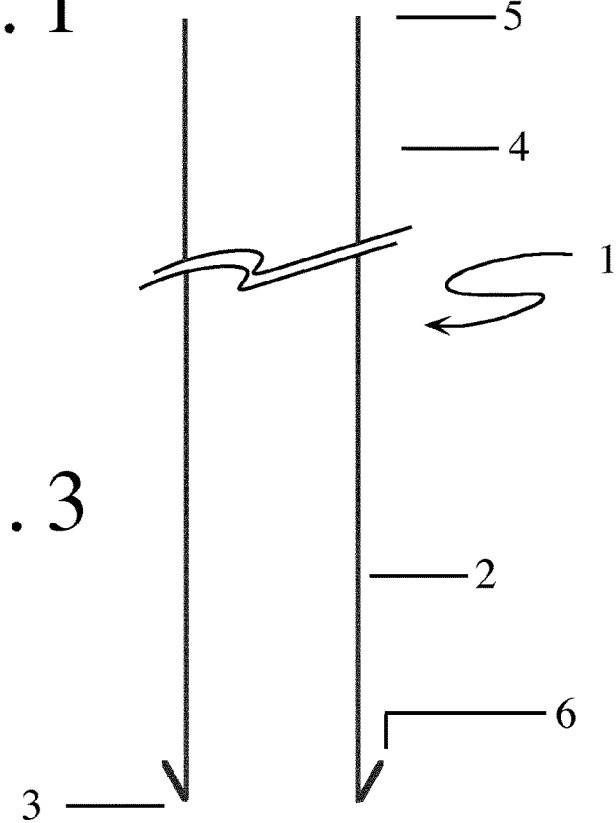
FIG. 3 is a longitudinal cross-sectional view of an anastomosis prosthesis.

The invention is comprised of a self-fixing prosthesis and an instrument for creating an end-to-side anastomosis with the prosthesis. Schematic illustrations of the invention are shown in FIGS. 1-3. The prosthesis is a tubular member 1 with a leading end 2 limited by a leading edge 3, and a trailing end 4 limited by a trailing edge 5.

Throughout the description, the adjective "leading" identifies the end or edge of an object, such as a prosthesis or device, that precedes the rest of said object, when said object is being introduced into another object such as the human body. Thus, the directionally describing expressions "leading" and "trailing" are herein used in the context of the direction of attachment of the tubular member to an organ, such as a blood vessel. The leading end is the end that is first inserted to the body and organ.

The leading end 2 of the prosthesis is radially compressible. The leading edge 3 of the prosthesis is provided with one or more flexible anchoring members 6 ("radial anchors"). The radial anchors 6 are initially directed outwards, in relation to the longitudinal direction of the tubular member 1, and towards the trailing end 5 of the prosthesis. In other words, the radial anchors 6 are initially arranged at an acute angle on the outside of the tubular member 1, and generally pointing in the direction of the trailing end rather that in the direction of insertion. The insertion procedure will be described in more detail below.

In the preferred embodiment of the invention, the leading end 2 is elliptical in cross-section perpendicular to the longitudinal axis of the prosthesis, and the plane defined by the leading edge 3 is not perpendicular to the longitudinal axis of the prosthesis (as seen for example in FIG. 4). In an alternative embodiment of the prosthesis, the leading end 2 is oval in cross-section perpendicular to the longitudinal axis of the prosthesis. In an alternative embodiment of the prosthesis, the leading end 2 is circular in cross-section perpendicular to the longitudinal axis of the prosthesis. In an alternative embodiment of the prosthesis, the leading end 2 is non-circular in cross-section perpendicular to the longitudinal axis of the prosthesis. In an alternative embodiment of the invention, the plane defined by the leading edge 3 is perpendicular to the longitudinal axis of the prosthesis.

In a preferred embodiment of the prosthesis, the leading end 2 is radially compressible and plastic, i.e. has plastic characteristics. On application of centripetal radial force of appropriate magnitude, the leading end 2 will be radially compressed. On removal of the centripetal force, the leading end 2 remains essentially unchanged in size. The compressed leading end 2 can be expanded to its nominal radial size by the intraluminal application of centrifugal force of appropriate magnitude. In an alternative embodiment of the prosthesis, the leading end 2 is radially resilient. On application of centripetal radial force of appropriate magnitude, the leading end 2 gets radially compressed. On removal of the centripetal force, the leading end 2 expands spontaneously to its nominal radial size.

The radial anchors 6 are preferably two or more arranged equally around the circumference of the leading edge 3. Each individual radial anchor can be provided as an essentially round wire or as strips cut from a tubular member. In the preferred embodiment of the prosthesis, the radial anchors 6 are structurally continuous with the leading edge 3 of the prosthesis. One example of such an arrangement is providing a lasercut tubular member with protruding anchoring members cut from the end of the tubular device.

In an alternative embodiment of the prosthesis, the radial anchors 6 are attached to the leading edge 3 of the prosthesis. In an alternative embodiment of the invention, the leading end 2 of the prosthesis is provided with a reversibly compressible, snugly fitting collar ("anchor collar") 7, with a leading edge 9 and a trailing edge 8. The leading edge 9 of the anchor collar 7 is flush with the leading edge 2 of the prosthesis (FIG. 5a). The radial anchors 6 are structurally continuous with the leading edge 9 of the anchor collar 7. In an alternative embodiment of the prosthesis, the radial anchors 6 are attached to the leading edge 9 of the anchor collar 7. In an alternative embodiment of the prosthesis, the leading edge 9 of the anchor collar 7 is not flush with the leading edge 3 of the prosthesis, such that the prosthesis protrudes slightly through the anchor collar 7 (FIG. 5b).

In another embodiment of the prosthesis, the leading end 2 is provided with an external coaxial expandable ring ("sealing ring") (10). The sealing ring is plastic. In an alternative embodiment of the prosthesis, the sealing ring 10 is radially compressible and plastic. In an alternative embodiment of the prosthesis, the sealing ring 10 is elastic. In an alternative embodiment of the prosthesis, the sealing ring 10 stimulates clotting of blood. In an alternative embodiment of the prosthesis, the sealing ring 10 is made of, or is coated with a material that increases in volume on exposure to fluids such as for example hydrogels. In one embodiment of the prosthesis, the sealing ring 10 encircles the radial anchors 6 (FIG. 6a). It is dimensionally matched to the compressed prosthesis such that it is held in position by friction, but is nonetheless movable along the long axis of the prosthesis. In an alternative embodiment of the invention, the sealing ring 10 is larger than the compressed prosthesis in cross-section (FIG. 6b), such that it is not held to the prosthesis by friction, but is prevented from moving to the leading end 2 of the prosthesis by the radial anchors 6.

In an alternative embodiment of the prosthesis, the trailing end 4 is radially compressible and plastic (FIG. 7). In an alternative embodiment of the prosthesis, the trailing end 4 is radially resilient.

One embodiment of the instrument for performing an anastomosis with radially compressible prosthesis (first deployment instrument) (FIG. 8) is comprised of a tubular member 12 (deployment catheter) and a coaxial linear flexible member 13 (needle wire). The deployment catheter 12 has a leading end 14 limited by a leading edge 15, a shaft 16 and a trailing end 17. The trailing end 17 of the deployment catheter 12 is provided with a means 18 for reversibly securing the needle wire 13, such as a Tuohy-Borst valve. The leading end of the deployment catheter 12 is radially expandable. The shaft 16 of the deployment catheter 12 is provided with a means to expand the leading end 14. The needle wire 13 has a leading end 19 limited by a leading tip 20 and a shaft 21, and can be moved along the longitudinal axis of the deployment catheter 12. The leading end 19 is more flexible than the shaft 21. The leading tip 20 of the needle wire 13 is shaped such that it can perforate an organ, such as a blood vessel.

Figure 9:
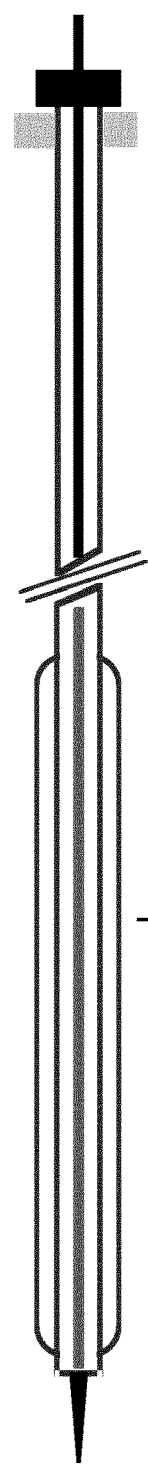

In the preferred embodiment of the first deployment instrument, the leading end 14 of the deployment catheter 12 is provided with a balloon 22 ("balloon deployment catheter") (FIG. 9). The shaft 16 of the deployment catheter is provided with a channel that allows the balloon 22 to be inflated.

Figure 10:
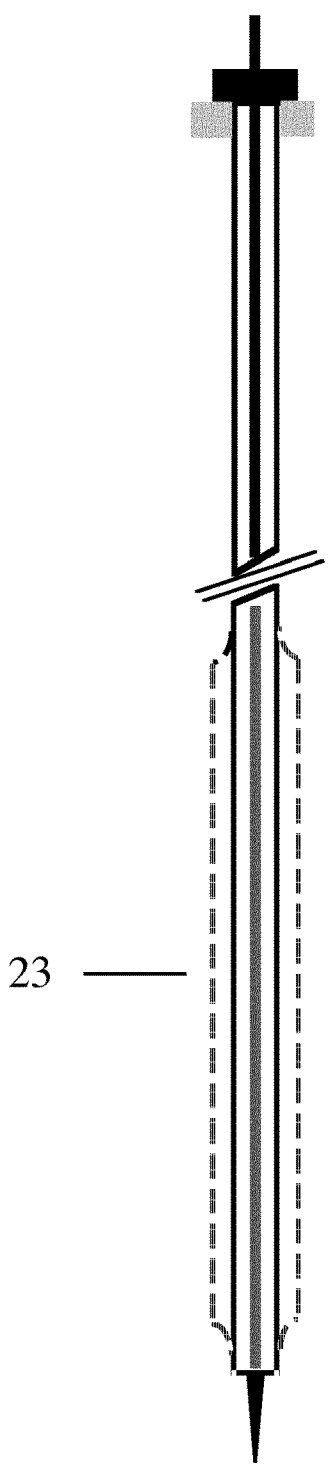

In an alternative embodiment of the first deployment instrument, the leading end 14 of the deployment catheter 12 is provided with an expandable basket like structure 23 (basket deployment catheter) (FIG. 10). The shaft 16 is provided with means to expand the basket.

In an alternative embodiment of the first deployment instrument (FIG. 11), the deployment catheter 12 is partially enclosed within a coaxial tubular member 24 ("inner sheath"), with a leading end 25 and a trailing end 26. The inner sheath 24 is encircled at its leading end by a sealing ring 10. The sealing ring 10 is dimensionally matched to the inner sheath 24, such that the it is held in position on the sheath 24 by friction, but is movable along the long axis of the of the inner sheath 24. The inner sheath 24 is partially enclosed within a second coaxial member 27 (pusher), such that the sealing ring 10 can be moved to the leading end 25 of the inner sheath with the pusher 27.

One embodiment of the instrument for performing an anastomosis with the prosthesis 31 (second deployment instrument) (FIG. 12) is comprised of a first tubular member 32 ("carrier catheter"), a coaxial second tubular member 33 ("protective sheath") that partially encloses the first tubular member 32 and a needle wire 13. The carrier catheter 32 has a leading end 34 limited by a leading edge 35, a shaft 36 and a trailing end 37. The trailing end 37 of the carrier catheter 32 is provided with a means 38 for reversibly securing the shaft of the needle wire 13, such as a Tuohy-Borst valve. The protective sheath 33 has a leading end 39 limited by a leading edge 40, a shaft 41 and a trailing end 42. The sheath 33 can accommodate the prosthesis, when the prosthesis is mounted on the carrier catheter 32.

In an alternative embodiment of the second deployment instrument 31 (FIG. 13), the protective sheath 33 is provided with a sealing ring 10 at its leading end 39. The ring 13 is dimensionally matched to the protective sheath 33, such that it is held in position by friction, but is nonetheless movable along the long axis of the protective sheath 33. The protective sheath 33 is partially enclosed within a coaxial tubular member 43 ("pusher"), with a leading end 44 and a trailing end 45, such that the sealing ring 13 can be moved to the leading end 39 of the protective sheath 33 with the pusher 43.

In an alternative embodiment of the invention (FIG. 14), the instrument for deploying the prosthesis is provided with a deployment guide 46 comprised of a first tubular member 47 (guide sheath), a coaxial second tubular member 48 that is partially enclosed within the first tubular member (guide pusher), and a sealing ring 13 that is completely enclosed within the first tubular member 47. The guide sheath has a leading end 49 limited by a leading edge 50, and a trailing end 51. The guide pusher 48 has a leading end 52 limited by a leading edge 53, and a trailing end 54, and can accommodate the instrument for deploying the prosthesis. The sealing ring 10 is dimensionally matched to the lumen of the guide sheath 47, such that it is held in place within the guide sheath 47 by friction, but can be moved towards the leading end 49 of the guide sheath 47 with the guide pusher 48. The sealing ring 10 can accommodate the instrument for deploying the prosthesis.

In the preferred embodiment of the invention, the leading end 19 of the needle wire 21 describes a curve when it is not constrained (FIG. 15). In an alternative embodiment of the invention, the needle wire is hollow along its entire length.

It is understood that the modifications to the prosthesis and deployment instrument that have been described in the preceding paragraphs may be incorporated singly or in various combinations not described above.

Figure 16:
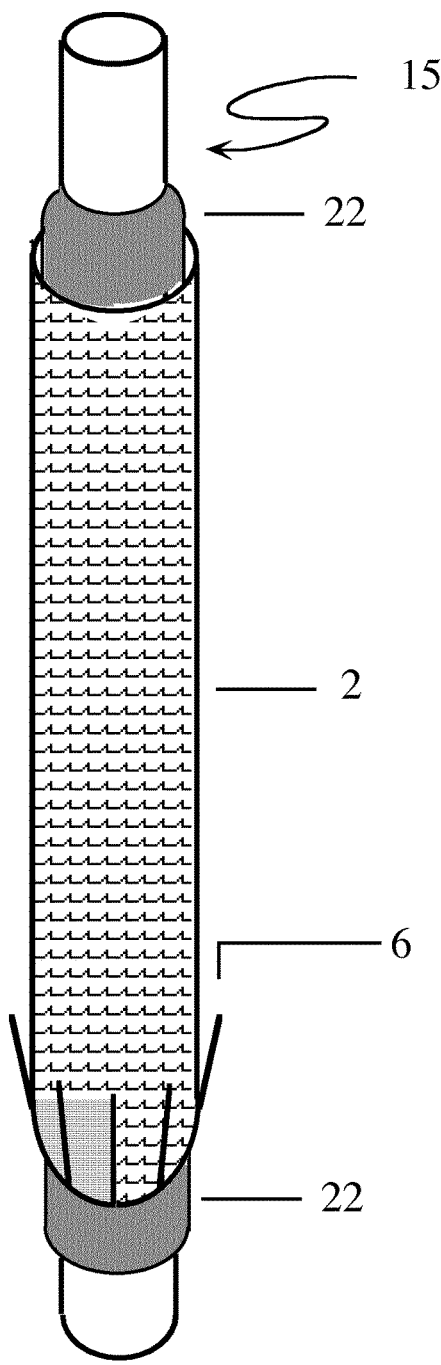
FIGS. 16, 17 represent perspective views of the leading end of an anastomosis prosthesis mounted on a deploying instrument.
Figure 17:
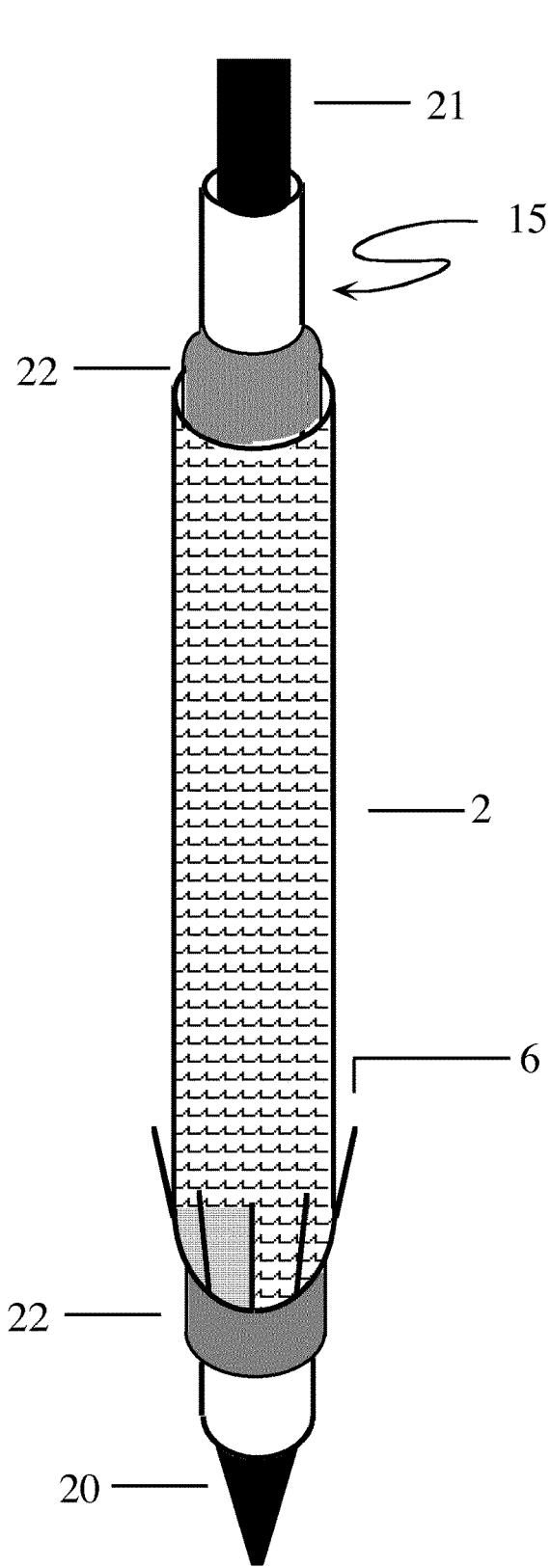

In the following several embodiments of the invention and exemplary procedures of use are described. Performance of an end-to-side anastomosis to the aorta is described to illustrate one of the envisaged uses of the invention. It does not limit in any way the scope of its application as set forth in this patent application. It is anticipated that the prosthesis will be mounted on the deployment instrument at the site of manufacture FIG. 16 illustrates how the prosthesis will be mounted on a deployment instrument. The needle wire 13 is omitted from figures in which it does not contribute anything of importance.

Figure 25:
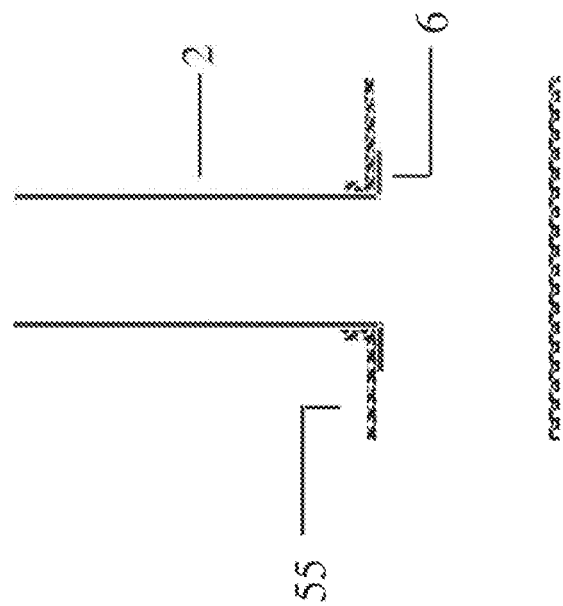
Figure 24:
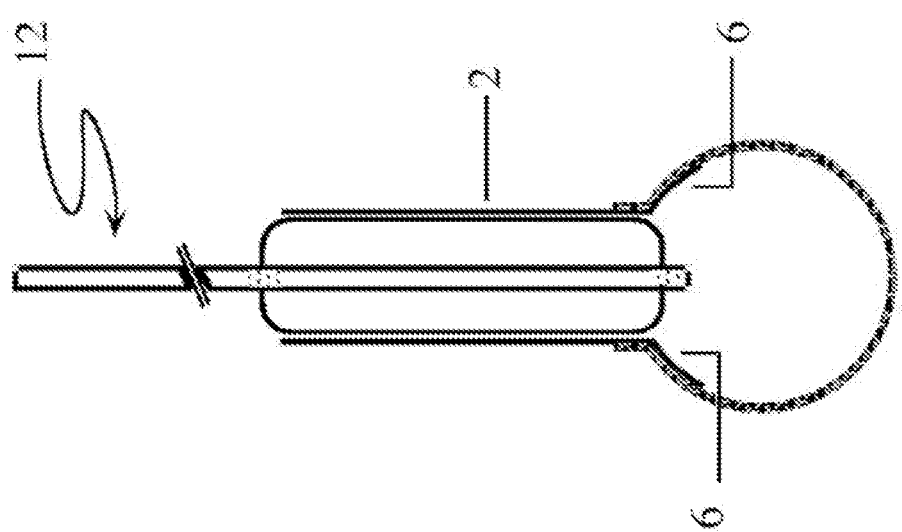

FIGS. 17-25 illustrate performance of the anastomosis with a radially compressible, plastic prosthesis using a deployment instrument incorporating a balloon deployment catheter 22. The site for anastomosis is selected after visual inspection, or ultrasonographic examination of e.g. an aorta 55. The needle wire 21 is advanced through the deployment balloon catheter 22. Once the leading tip 20 protrudes through the catheter 22, the needle wire 21 is secured to the trailing end of the catheter 22. The catheter and needle wire are introduced into the aorta. The needle wire 21 is released from the trailing end of the catheter 22 and advanced till its shaft 21 has entered the aorta 55 (FIG. 19). (This step could preferably be monitored with ultrasonography.) The deployment catheter is advanced until all the radial anchors 6 are inside the aorta (FIG. 20). The balloon is partially expanded, as shown in FIG. 21. The balloon deployment catheter 22 and prosthesis are slowly withdrawn, until resistance is felt, indicating that the radial anchors 6 and the leading edge 3 of the prosthesis are substantially flush with the luminal surface of the aorta 55 (FIG. 22). The balloon is inflated to its nominal diameter expanding the prosthesis. FIG. 23 shows the inflated balloon in a view along a longitudinal cross-section of the aorta, and FIG. 24 shows how the same step from a view perpendicular to a longitudinal axis of the aorta. The balloon is thereafter deflated, and the balloon deployment catheter is removed (FIG. 25). Tissue adhesive is applied at the junction of the artery and the prosthesis to reinforce the anastomosis if desired.

The arrangement of the radial anchors 6 being initially arranged at an acute angle pointing back towards the trailing end, as can be seen in the figures, has the advantage of facilitating entry of the deployment assembly into the organ of choice.

As the device is deployed, the radial anchors 6 are bent to an angle essentially perpendicular to the longitudinal axis of the tubular member, as can be seen in e.g. FIG. 22, such that the radial anchors 6 are flush against the inner organ wall. This ensures satisfactory anchoring of the tubular device, yet ensures that only very little non-endothelial surface is exposed to blood As shown above, at least the leading end of the tubular device is reversibly radially compressible. This ensures easy deployment and secure anchoring of the tubular device. This allows the anastomosis to be performed through a puncture in the wall of an artery in contrast to the incision required with devices described thus far.

Figure 28:
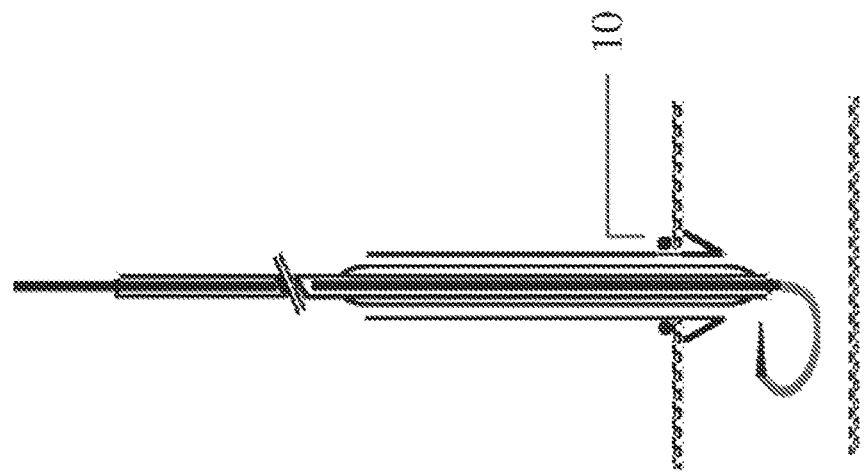
Figure 27:
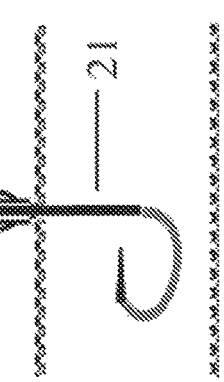
Figure 26:
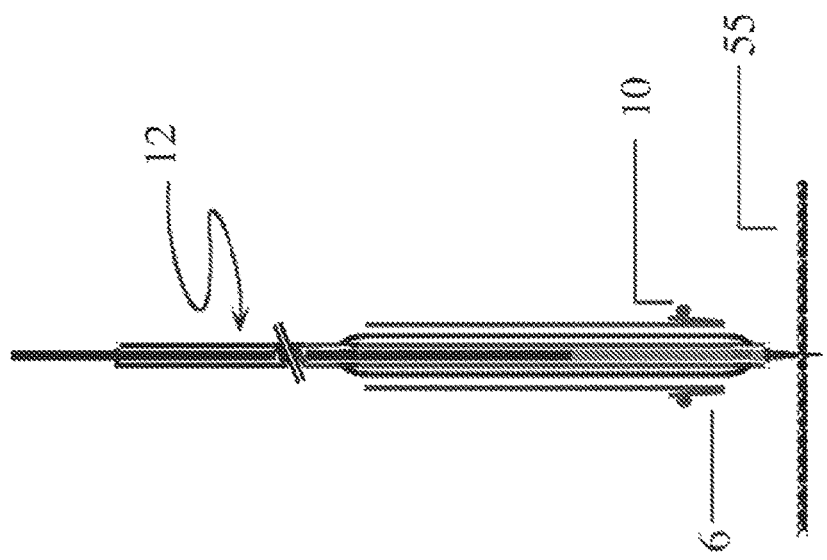

FIGS. 26-32 illustrate how performance of the anastomosis with a radially compressible, plastic prosthesis incorporating a sealing ring 10 differs from the procedure described above. When the balloon deployment catheter 22 and prosthesis are advanced into the aorta 55, the sealing ring 10 is retained on the aortic wall (FIG. 28). The ring is held in place when deployment catheter 15 and the prosthesis are withdrawn. The seal is then released. When the balloon is inflated, the sealing ring is expanded securing it to the prosthesis, thereby sealing the anastomosis (FIG. 32). If the non-expanded sealing ring is larger than the compressed prosthesis in cross-section, the seal need not be held in place. As the sealing ring is not secured to the prosthesis by friction, it remains in place at the anastomosis site when the deployment catheter 15 and the prosthesis are withdrawn.

FIGS. 33-35 illustrate how performance of the anastomosis with a radially compressible, plastic prosthesis and a deployment instrument incorporating a sealing ring differs from the procedure described above. Once all the radial anchors 6 are within the aorta 55, the inner sheath 24 is withdrawn out of the aorta 55, exposing the radial anchors (6). The pusher 27 is advanced to the sealing ring 10 to retain it at the anastomosis (FIG. 33). The deployment catheter and prosthesis are withdrawn until the radial anchors 6 are flush with the luminal surface of the aorta 55 (FIG. 34). The inner sheath 24 is then withdrawn until the entire prosthesis is outside the sheath. The pusher 27 is then withdrawn until it no longer encloses the prosthesis (FIG. 35). The prosthesis is expanded as described above, securing the sealing collar to the anastomosis.

Figure 38:
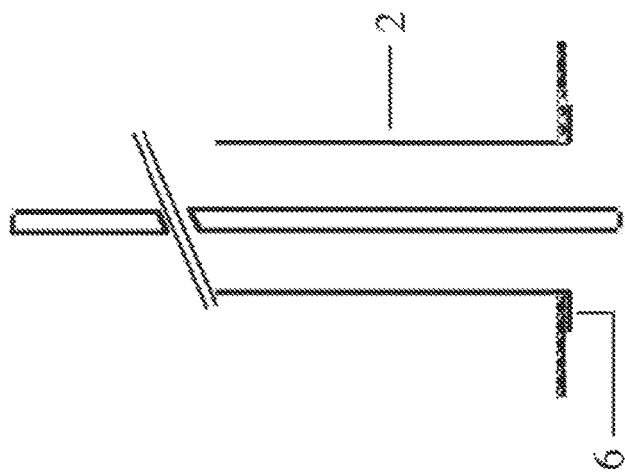
Figure 37:
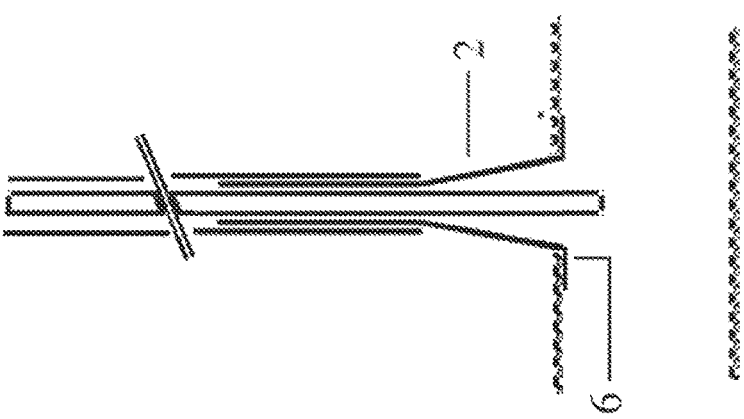
Figure 36:
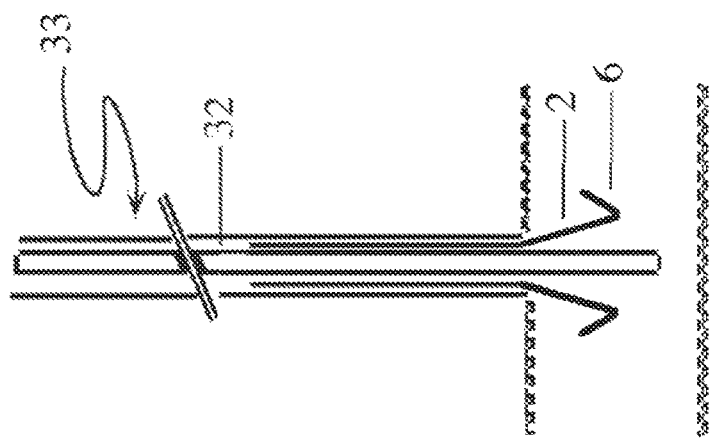

FIGS. 36-38 illustrate how performance of the anastomosis with a radially compressible, radially resilient prosthesis and a second deployment instrument differs from the procedures described above. Once all the radial anchors 6 are within the aorta 55, the protective sheath 33 is withdrawn out of the aorta 55 to allow the prosthesis to partially expand (FIG. 36). The carrier catheter 34 and prosthesis are withdrawn till the radial anchors 6 are flush with the luminal surface of the aorta 55 (FIG. 37). The protective sheath 33 is withdrawn to allow the entire prosthesis to expand (FIG. 38). The protective sheath 33 and the carrier catheter 24 are then removed.

Figure 41:
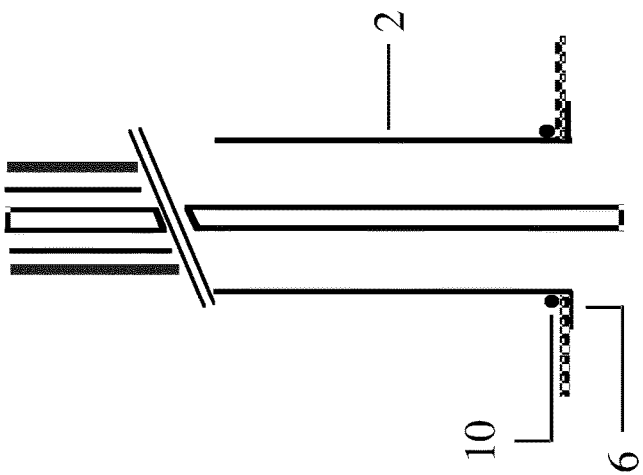
Figure 40:
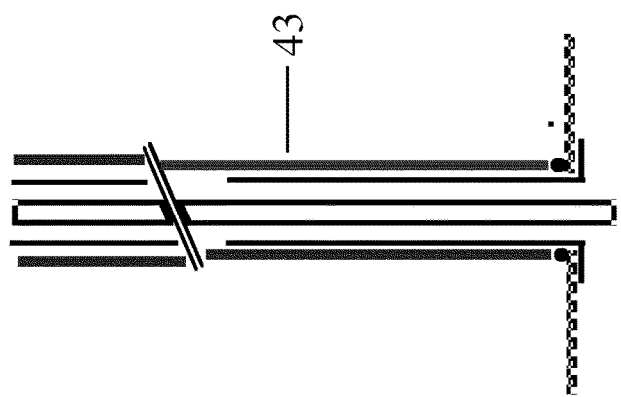
Figure 39:
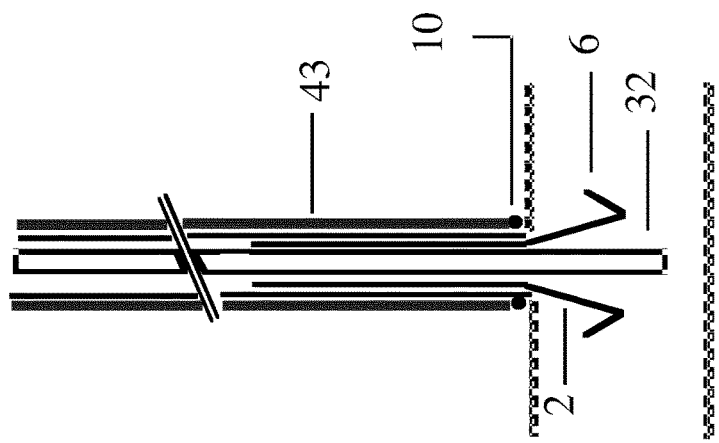

FIGS. 39-41 illustrate how performance of the anastomosis with a radially compressible, radially resilient prosthesis and sealing ring incorporated in deployment instrument differs from the procedure described above. Once all the anchoring rings 6 are within the aorta, the pusher 43 is advanced to the sealing ring to keep it at the aortic wall, and the protective sheath 33 is withdrawn out of the aorta 55 to allow the prosthesis to partially expand (FIG. 39). The protective sheath 33 is withdrawn until the prosthesis is outside the sheath (FIG. 40) is then withdrawn. The pusher is then withdrawn to allow the prosthesis and the sealing ring to expand (FIG. 41).

An alternative way of performing an anastomosis with the prosthesis is as follows. The site for anastomosis is selected after visual inspection, or ultrasonographic examination of the aorta. A sealing ring is placed at the site and held in place. A compressible plastic or a compressible resilient prosthesis is then deployed as described above.

The invention claimed is:

1. An anastomosis prosthesis for end-to-side connection of a vascular graft to a blood vessel, said prosthesis comprising a tubular member with a leading end comprising a leading edge, and a trailing end comprising a trailing edge, wherein the leading end of the tubular member is reversibly, radially compressible, the leading edge of the tubular member is provided with one or more radially outwardly directed flexible, linear anchoring members, wherein said anchoring members are initially arranged at an angle in relation to a longitudinal axis of the tubular member and such that said anchoring members point in the direction of the trailing end of the tubular member, and the leading end of the tubular member is provided with a coaxial, outer expandable ring, the ring being flush with the leading edge of the tubular member, and the ring encircling said anchoring members.

2. An anastomosis prosthesis according to claim 1, wherein the leading end of the tubular member is not circular in cross-section perpendicular to the long axis of the tubular member.

3. An anastomosis prosthesis according to claim 1, wherein the plane defined by the leading edge of the tubular member is not perpendicular to the long axis of the tubular member.

4. An anastomosis prosthesis according to claim 1, wherein the leading end is plastic, such that said leading end can be expanded to a nominal radial size, by exposing it to centrifugal force.

5. An anastomosis prosthesis according to claim 1, wherein the leading end is radially resilient, such that, said leading end spontaneously expands to a nominal radial size, when it is no longer radially constrained.

6. An anastomosis prosthesis according to claim 1, wherein the leading end is plastic, such that said leading end expands to a nominal radial size, when the local thermal environment is appropriately altered.

7. An anastomosis prosthesis according to claim 1, wherein the outer surface of the trailing end of the tubular member is not smooth.

8. An anastomosis prosthesis according to claim 1, wherein the trailing end of the tubular member is reversibly, radially compressible.

* * * * *